United States Patent
Schreiber et al.

(10) Patent No.: US 6,613,338 B1
(45) Date of Patent: Sep. 2, 2003

(54) COSMETIC AND SKIN CARE STICKS WITH HIGH WATER CONTENTS

(75) Inventors: Jörg Schreiber, Hamburg (DE); Khiet Hien Diec, Hamburg (DE); Florian Wolf, Hamburg (DE); Manfred Klier, Aumühle (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/284,369

(22) PCT Filed: Oct. 17, 1997

(86) PCT No.: PCT/DE97/02401

§ 371 (c)(1),
(2), (4) Date: Apr. 14, 1999

(87) PCT Pub. No.: WO98/17232

PCT Pub. Date: Apr. 30, 1998

(30) Foreign Application Priority Data

Oct. 19, 1996 (DE) .......................................... 196 43 237

(51) Int. Cl.[7] .............................. A61K 6/00; A61K 7/00; A61K 7/42; A61K 7/025; A61K 7/021

(52) U.S. Cl. .......................... 424/401; 424/63; 424/59; 424/64; 514/938; 514/941

(58) Field of Search .......................... 424/59, 64, 401, 424/63; 514/938, 941

(56) References Cited

U.S. PATENT DOCUMENTS 4,725,431 A * 2/1988 Hourihan et al. ............. 424/66

FOREIGN PATENT DOCUMENTS

EP 0522624 * 1/1993

* cited by examiner

Primary Examiner—Thurman K. Page
Assistant Examiner—S. Howard
(74) Attorney, Agent, or Firm—Norris McLaughlin & Marcus

(57) ABSTRACT

Lipsticks, antiacne sticks, sunscreen sticks and eyeshadow sticks, with a high water content, characterized in that they comprise (a) a lipid phase, which comprises
  (a1) at least one oil component
  (a2) at least one wax component
  (a3) optionally other substances soluble or dispersible in the lipid phase,
(b) an aqueous phase, which comprises
  (b1) from 30 to 85% by weight of water, based on the total weight of the stick composition and
  (b2) if desired, substances soluble or dispersible in water,
(c) at least one active ingredient or several chosen from the active ingredients known for lipsticks, antiacne sticks, sunscreen sticks and eyeshadow sticks,
(d) a W/O emulsifier or a mixture of two or more W/O emulsifiers,
(e) one or more stabilizers, chosen from the group of substances of the general structure A—B—A', where A and A' are identical or different hydrophobic organic radicals, and B is a hydrophilic group,
(f) if desired, further surface-active substances as coemulsifiers, and also, if desired, stabilizers and further customary cosmetic and/or pharmaceutical auxiliaries, active ingredients and/or additives.

17 Claims, No Drawings

COSMETIC AND SKIN CARE STICKS WITH HIGH WATER CONTENTS

The present invention relates to cosmetic sticks which are characterized by a high water content and which, as advantageous embodiments, can be W/O emulsions. In particular, the present invention relates to lipsticks, preferably lipcare sticks, but also decorative lipsticks, and also stick formulations which are suitable, for example, for use against acne. As other advantageous embodiments, the present invention relates to sunscreen sticks, eyeshadow sticks and similar products.

From a technical viewpoint, most stick formulations are anhydrous fatty mixtures of solid or semisolid waxes and liquid oils, the ultrapure paraffin oils and waxes forming the lipstick base. Hydrous preparations are also known, which are sometimes also in the form of W/O emulsions.

The ideal profile of requirements includes smooth application of cosmetic or pharmaceutical sticks without substantial friction. Moreover, such a formulation must also satisfy the requirements that the stick in question must be resistant to breaking and to temperature and the formulation must not lose oil.

A lipstick in particular, even when pressed lightly, should leave a non-greasy, dull or sticky, but nevertheless highly adherent lipid film on the lips. This lipid film should make the lips smooth and soft.

If cosmetic or pharmaceutical sticks are to comprise certain active ingredients, it is conceivable that the other constituents are incompatible with the active ingredients. This is frequently the case particularly when it is intended that the cosmetic sticks be used as sunscreen sticks, and, in particular, water-soluble light protection filters are to be present in relatively large amounts in the stick, or when, in the preparation of an antiacne stick, water-soluble antiacne active ingredients are to be incorporated in amounts known to the person skilled in the art.

For reasons of compatibility, it is always preferable, even when using substances which are acceptable per se, to keep the corresponding use concentrations of such active ingredients as low as possible.

An object of the present invention was thus to develop preparations which are suitable as bases for cosmetic light protection filters, physical light protection filters, antiacne active ingredients and vitamins, and which do not have the disadvantages of the prior art. Furthermore, it was also an object of the invention to develop cosmetic bases which are characterized by good skin compatibility.

Customary prior art bases for stick preparations are, for example, liquid oils (e.g. paraffin oils, castor oil, isopropyl myristate), semisolid constituents (e.g. vaseline, lanolin), solid constituents (e.g. beeswax, ceresin and microcrystalline waxes or ozokerite) and high-melting waxes (e.g. carnauba wax, candelilla wax).

Prior art lipsticks containing paraffins and beeswax are described in "Kosmetik, Entwicklung Herstellung und Anwendung kosmetischer Mittel" [Cosmetics, development, preparation and use of cosmetic compositions], p. 105, editor W. Umbach, Georg Thieme Verlag, Stuttgart-New York, 1988.

However, the prior art has a number of disadvantages. These include the fact that water-soluble active ingredients are frequently insufficiently fat-soluble to be incorporated to a significant extent into the cosmetic bases. On the other hand, a certain water content would indeed be desired to increase the compatibility of the cosmetic stick with the human skin. In addition, sticks with very high water contents cannot be prepared in accordance with the prior art because the water is incompatible with the hydrophobic oil/wax/emulsifer matrix.

For an antiacne stick, for example, it would, however, be particularly advantageous if the proportion of fat-soluble constituents were as low as possible.

The skin of the lips has only a very thin horny layer. There are no sweat glands on the lips, and only few sebaceous glands. The skin of the lips is therefore virtually free from lipids and is prone to drying out, particularly in cold and dry weather. It is possible for small cracks to form in the skin, and the susceptibility of the lips to chemical, physical and microbial factors (e.g. foods, sunlight, Herpes simplex viruses) increases.

To prevent this from happening is the purpose of lipcare sticks. These products usually contain a high proportion of waxes and fatty components which form a covering layer over the lips following application.

In the preparations for lipcare sticks, it is possible to additionally incorporate active ingredients which are required for lipcare or for lip protection e.g. vitamins, moisturizers, light protection agents, covering pigments etc.

The dermis of the lips is provided with papillae which are well supplied with blood and extend up to just below the surface of the lips. This is why the lips are red and distinct with regard to colour from the remaining facial skin to a greater or lesser extent depending on the skin colour of the person in question. A stylistic element of decorative cosmetics is to match the colour of the lips to the type of person using suitable cosmetics.

Products of this type are decorative lipsticks into which a very wide range of colour pigments can be incorporated. These sticks, too, contain high proportions of waxes and fatty components which form a covering lipid layer over the lips following application.

However, the purpose of this layer is not primarily to protect the skin of the lips from drying out. The lipid layer serves in this case as a base, which adheres to the lips, for the incorporated pigment materials; the pigments themselves cannot be applied to the lips without such a base for various reasons.

It is also possible to combine the properties of conditioning and decorative lipsticks with one another, i.e. to incorporate conditioning or protective substances into decorative lipsticks.

Since both conditioning and predominantly decorative lipsticks in the prior art sometimes have serious shortcomings, a further object of the present invention was to remedy these shortcomings.

Because of the high sensitivity of the lip region, in particular to ultraviolet radiation as a result of the virtually complete absence of pigments, it is advisable, at least where UV exposure is increased, such as in high mountains, to provide the lip region with protection against UV radiation in the form of corresponding stick light protection formulations. Especially in prior art stick preparations, inorganic pigments are often used as UV absorbers or UV reflectors to protect the lip region against UV rays. These are, in particular, oxides of titanium, but also sometimes of zinc, iron, zirconium, silicon, manganese, aluminium, cerium and mixtures thereof, and also modifications.

A significant shortcoming of the prior art formulations is that, inter alia, because of the low water contents of emulsion sticks which are acceptable per se, it was virtually impossible to incorporate water-soluble UV filter substances into such formulations. A further object of the present invention was thus to make available sticks containing exclusively water-soluble UV filters or water-dispersible pigments (for example titanium dioxide), or combinations of water-soluble and fat-soluble UV filters.

DBP 23 35 549 discloses a process for the preparation of a cosmetic stick based on a W/O emulsion. According to this teaching, a polyhydroxy compound and a nonionogenic, surface-active compound are used to prepare a gel, which is mixed with a cosmetic base, and water is emulsified into the mixture.

However, using this process it is not possible to prepare sticks which satisfy the universal requirements demanded of a cosmetic stick. Furthermore, since this process is not a one-step process, it is notable for further disadvantages.

DE-A 41 28 748 describes cosmetic sticks which are characterized in that they are emulsions and comprise, as essential ingredients, beeswax, one or more esters of a saturated carboxylic acid having 20–40 carbon atoms and a saturated alcohol having 14–34 carbon atoms, water, and optionally further lipids and/or customary auxiliaries and additives. Although these preparations do have advantageous properties, certain disadvantages must also be accepted.

U.S. Pat. No. 4,719,103 describes an antiperspirant stick based on a W/O emulsion which contains a high water content, which is characterized by a content of volatile silicone components, a solid alkanol and polyglycerol fatty acid esters, for example polyglyceryl isostearate, as emulsifier. U.S. Pat. Nos. 4,704,271 and 4,725,431 describe similar preparations.

GB-A 2 162 439 describes paraffin-containing sticks which comprise a high water content, the emulsifiers being chosen from the group of metal salts.

In view of the above, it was surprising and could not have been predicted that cosmetic sticks, in particular those chosen from the group consisting of lipsticks, antiacne sticks, sunscreen sticks and eyeshadow sticks, characterized in that they comprise
 (a) a lipid phase, which comprises
  (a1) at least one oil component
  (a2) at least one wax component
  (a3) optionally other substances soluble or dispersible in the lipid phase,
 (b) an aqueous phase, which comprises
  (b1) from 30 to 85% by weight of water, based on the total weight of the stick composition and
  (b2) if desired, substances soluble or dispersible in water,
 (c) if desired, one or more active ingredients, chosen from the active ingredients known for lipsticks, antiacne sticks, sunscreen sticks and eyeshadow sticks,
 (d) at least one W/O emulsifier or a mixture of two or more W/O emulsifiers,
 (e) one or more stabilizers, chosen from the group of substances of the general structure A—B—A', where A and A' are identical or different hydrophobic organic radicals, and B is a hydrophilic group,
 (f) if desired, further surface-active substances as coemulsifiers, and also, if desired, further stabilizers and further customary cosmetic and/or pharmaceutical auxiliaries, active ingredients and/or additives,
overcome the disadvantages of the prior art.

It was surprising that the novel preparations permit the incorporation of large amounts of water, even when only small amounts of emulsifiers used according to the invention are present. The release in particular of water-soluble active ingredients is significantly increased compared with conventional preparations. One example, is the increase in the light protection factor, which is more effective according to the invention in relatively low concentration than the preparations of the prior art, i.e. for example compared with W/O sticks with a low water content or compared with water-free suspension sticks.

However, the cosmetic properties of the novel water-rich sticks have also proven to be clearly better than those of the prior art. For example, even without further additions, a pleasant cooling effect on the skin can be achieved by mere application, which is pleasantly notable particularly in the case of use as sunscreen stick, antiacne stick and lipstick.

In the case of use as lipstick, for moistening the skin or as antiacne stick, clear improvements over the prior art are also notable. For example, when preparing these sticks it is possible to use water-dispersible titanium dioxide.

The preparation of the novel sticks is very simple since it involves a one-step process in which, for example, the aqueous phase is added to the hot lipid phase and then cooled to room temperature.

In addition, the novel process is characterized by the fact that, for the preparation of the novel sticks, it is possible to use a large number of emulsifiers or oil components.

The W/O emulsifier or the W/O emulsifiers from the substance group A—B—A' used according to the invention is or are advantageously chosen according to the invention from the group of substances of the general formula

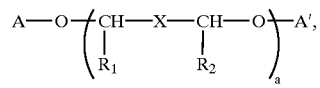

where
 A and A' are identical or different hydrophobic organic radicals,
 a is a number from 1 to 100, preferably from 2 to 60, in particular from 5 to 40,
 X is a single bond or the group

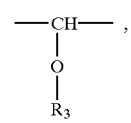

$R_1$ and $R_2$ independently of one another are chosen from the group consisting of H or methyl, but such that the two radicals are not methyl at the same time,
 $R_3$ is chosen from the group consisting of H and the branched and unbranched, saturated and unsaturated alkyl and acyl radicals having 1–20 carbon atoms.

The structural formula must not be interpreted as meaning that because of the index a, all of the radicals $R_1$, $R_2$ or $R_3$ represented in the brackets must in each case be identical throughout the entire molecule. Instead, these radicals can be freely chosen in each of the a fragments

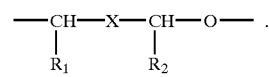

The radicals A and A' are advantageously chosen from the group of branched and unbranched, saturated and unsaturated alkyl and acyl radicals and hydroxyacyl radicals having 10–30 carbon atoms and also from the group of hydroxyacyl groups joined together via ester functions, according to the formula

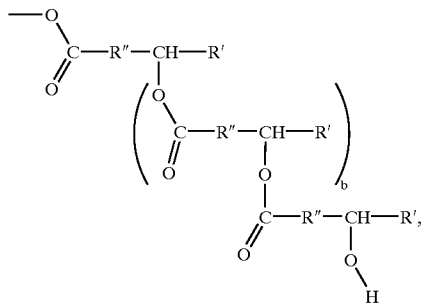

where R' is chosen from the group of branched and unbranched alkyl groups having from 1 to 20 carbon atoms, and R" is chosen from the group of branched and unbranched alkylene groups having from 1 to 20 carbon atoms, and b can assume numbers from 0 to 200.

Examples of W/O emulsifiers of the A—B—A' type which are to be used particularly advantageously for the purposes of the present invention are PEG-30 dipolyhydroxystearate, decaglyceryl heptaoleate, polyglyceryl-3 diisostearate, PEG-8 distearate, diglycerol dipolyhydroxystearate.

However, it is also possible according to the invention to choose the W/O emulsifier(s) from the group consisting of fatty alcohols having 8–30 carbon atoms, monoglycerol esters of saturated and/or unsaturated, branched and/or unbranched alkanecarboxylic acids having a chain length of 8–24, in particular 12–18, carbon atoms, diglycerol esters of saturated and/or unsaturated, branched and/or unbranched alkanecarboxylic acids having a chain length of 8–24, in particular 12–18, carbon atoms, triglycerol esters of saturated and/or unsaturated, branched and/or unbranched alkanecarboxylic acids having a chain length of 8–24, in particular 12–18, carbon atoms, polyglycerol esters of saturated and/or unsaturated, branched and/or unbranched alkanecarboxylic acids having a chain length of 8–24, in particular 12–18, carbon atoms and up to 10 glycerol units, monoglycerol ethers of saturated and/or unsaturated, branched and/or unbranched alcohols having a chain length of 8–24, in particular 12–18, carbon atoms, diglycerol ethers or saturated and/or unsaturated, branched and/or unbranched alcohols having a chain length of 8–24, in particular 12–18, carbon atoms, triglycerol ethers of saturated and/or unsaturated, branched and/or unbranched alcohols having a chain length of 8–24, in particular 12–18, carbon atoms, polyglycerol ethers of saturated and/or unsaturated, branched and/or unbranched alkanecarboxylic acids having a chain length of 8–24, in particular 12–18, carbon atoms and up to 10 glycerol units, propylene glycol esters of saturated and/or unsaturated, branched and/or unbranched alkanecarboxylic acids having a chain length of 8–24, in particular 12–18, carbon atoms, sorbitan esters of saturated and/or unsaturated, branched and/or unbranched alkanecarboxylic acids having a chain length of 8–24, in particular 12–18, carbon atoms, sorbitan esters of polyols, in particular of glycerol, pentaerythritol esters of saturated and/or unsaturated, branched and/or unbranched alkanecarboxylic acids having a chain length of 8–24, in particular 12–18, carbon atoms, methylglucose esters of saturated and/or unsaturated, branched and/or unbranched alkanecarboxylic acids having a chain length of 8–24, in particular 12–18, carbon atoms, polyglycerol methylglucose esters of saturated and/or unsaturated, branched and/or unbranched alkanecarboxylic acids having a chain length of 8–24, in particular 12–18, carbon atoms It can also be advantageous according to the invention for the abovementioned types of W/O emulsifiers to be additionally polyethoxylated and/or polypropoxylated, or for other polyethoxylated and/or polypropoxylated products to also be used, for example polyethoxylated, hydrogenated or nonhydrogenated castor oil, ethoxylated cholesterol.

Particularly advantageous W/O emulsifiers are glyceryl lanolate, glyceryl monostearate, glyceryl monoisostearate, glyceryl monomyristate, glyceryl monooleate, diglyceryl monostearate, diglyceryl monoisostearate, diglyceryl diisostearate, propylene glycol monostearate, propylene glycol monoisostearate, propylene glycol diisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, 2-ethylhexyl glycerol ether, selachyl alcohol, chimyl alcohol, polyethylene glycol (2) stearyl ether (steareth-2), glyceryl monolaurate, glyceryl monocaprinate, glyceryl monocaprylate, glyceryl sorbitan stearate, polyglyceryl-4 isostearate, polyglyceryl-2-sesquiisostearate, PEG-7 hydrogenated castor oil, PEG-40 sorbitan perisostearate, isostearyl diglyceryl succinate, PEG-5 cholesteryl ether.

The W/O emulsifier used according to the invention or the W/O emulsifiers used according to the invention, which conform(s) to the formula A—B—A', is or are advantageously present in concentrations of 0.1–25% by weight, it being possible and advantageous, however, to keep the content of emulsifiers low, for example up to 5% by weight, in each case based on the total weight of the composition. It is advantageous to choose the total concentration of the W/O emulsifiers, which also include those emulsifiers which do not conform to the formula A—B—A', to be no greater than about 25–30% by weight and not less than about 0.1% by weight, in each case based on the total weight of the preparations.

The stabilizers used for the purposes of the invention are, according to the invention, advantageously chosen from the group of substances of the general formula

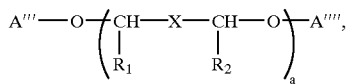

where

A''' and A'''' are identical or different hydrophobic organic radicals, a is a number from 1 to 100, preferably from 2 to 60, X is a single bond or the group

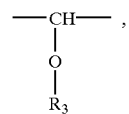

$R_1$ and $R_2$ independently of one another are chosen from the group consisting of H and methyl, but such that the two radicals are not methyl at the same time, $R_3$ is chosen from the group consisting of H and the branched and unbranched, saturated and unsaturated alkyl and acyl radicals having 1–20 carbon atoms.

The structural formula must not be interpreted to mean that, because of the index a, all of the radicals $R_1$, $R_2$ and $R_3$, represented in the brackets, must in each case be identical throughout the whole molecule. Instead, these radicals can be chosen freely in each of the a fragments

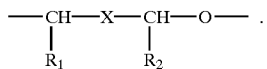

The radicals A''' and A'''' can be identical or different and are preferably chosen from the group

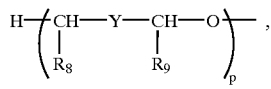

where $R_8$ and $R_9$ can be identical or different and are chosen from the group of saturated and unsaturated alkyl and acyl radicals having 1–30 carbon atoms, p is a number from 1 to 20, and Y is a single bond or the group

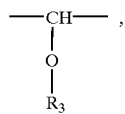

where $R_3$ is chosen from the group consisting of H and the branched and unbranched, saturated and unsaturated alkyl and acyl radicals having 1–30 carbon atoms.

A preferred stabilizer is the PEG-45/dodecyl glycol copolymer, which has the structure

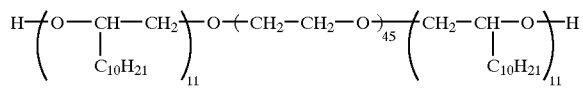

It is supplied by Akzo Nobel Chemicals GmbH under the name ELFACOS® ST 9. It is, however, also advantageous to use the corresponding PEG-22/dodecyl glycol copolymer.

In addition, the groups A''' and A'''' can, independently of one another, also be alkyl radicals or acyl radicals. Another particularly advantageous stabilizer is the methoxy-PEG-22-dodecyl glycol copolymer. It is supplied by Akzo Nobel Chemicals GmbH under the name ELFACOS® E 200.

The stabilizer or the stabilizers are advantageously present in concentrations of 0.01–25% by weight, it being possible and advantageous, however, to keep the content of stabilizers low, for example up to 5% by weight, in each case based on the total weight of the composition.

It is advantageous to choose stabilizers particularly when novel preparations are to comprise a high content of destabilizing substances, for example light protection filters. If the content of destabilizing substances is low, it is possible to dispense with the stabilizer.

The oil component or the totality of the oil components of the novel hydrous, cosmetic sticks should be liquid at room temperature, the wax component or the totality of the wax components should be solid at room temperature. It is advantageous to match the oil components and the wax components to each other such that the mixture of oil components and wax components without residual components, i.e. for example without an aqueous phase and without emulsifier, is solid at room temperature.

The oil component or the totality of the oil components of the novel hydrous, cosmetic sticks is preferably chosen from the group of esters of saturated and/or unsaturated, branched and/or unbranched alkanecarboxylic acids having a chain length of from 1 to 44 carbon atoms and saturated and/or unsaturated, branched and/or unbranched alcohols having a chain length of from 1 to 44 carbon atoms, from the group of esters of aromatic carboxylic acids and saturated and/or unsaturated, branched and/or unbranched alcohols having a chain length of from 1 to 30 carbon atoms, provided the oil component or the totality of the oil components is a liquid at room temperature. Such ester oils can then advantageously be chosen from the group consisting of isopropyl myristate, isopropyl palmitate, isopropyl stearate, oleate, n-butyl stearate, n-hexyl laurate, n-decyloleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semisynthetic and natural mixtures of such esters, e.g. jojoba oil.

In addition, the oil phase can advantageously be chosen from the group of branched and unbranched hydrocarbons, silicone oils, dialkyl ethers, the group of saturated or unsaturated, branched alcohols, and the fatty acid triglycerides, namely the triglycerol esters of saturated and/or unsaturated, branched and/or unbranched alkanecarboxylic acids having a chain length of from 8 to 24, in particular 12–18, carbon atoms. The fatty acid triglycerides can, for example, be advantageously chosen from the group of synthetic, semisynthetic and natural oils, e.g. olive oil, sunflower oil, soya oil, peanut oil, rapeseed oil, almond oil, palm oil, coconut oil, palm kernel oil and the like.

The oil phase is advantageously also chosen from the group consisting of 2-ethylhexyl isostearate, octyldodecanol, isotridecyl isononanoate, isoeicosane, 2-ethylhexyl cocoate, $C_{12-15}$-alkyl benzoate, capryl-capric triglyceride, dicaprylyl ether, ethylene glycol dioleate, di-(2-ethylhexyl)adipate.

The oil phase can also advantageously have a content of cyclic or linear silicone oils or consist entirely of such oils, although it is preferable to use, in addition to the silicone oil or silicone oils, an additional content of other oil phase components.

Cyclomethicone (octamethylcyclotetrasiloxane) is advantageously used as the silicone oil to be used according to the invention. However, it is also advantageous for the purposes of the present invention to use other silicone oils, for example hexamethyl cyclotrisiloxane, polydimethylsiloxane, poly(methylphenylsiloxane).

The oil components are preferably chosen from the group of esters of saturated branched alkanecarboxylic acids having a chain length of from 1 to 44 carbon atoms and saturated unbranched alcohols having a chain length of from 1 to 44 carbon atoms, provided the oil component or the totality of the oil components is a liquid at room temperature, and/or of esters of saturated unbranched alkanecarboxylic acids having a chain length of from 1 to 44 carbon atoms and saturated branched alcohols having a chain length of from 1 to 44 carbon atoms, provided the oil component or the totality of the oil components is a liquid at room temperature.

The oil components are particularly preferably chosen from the group of esters of saturated branched alkanecarboxylic acids having a chain length of from 14 to 44 carbon atoms and saturated branched alcohols having a chain length of from 14 to 44 carbon atoms, provided the oil component or the totality of the oil components is a liquid at room temperature.

Particularly advantageous oil components can be chosen from the group consisting of isotridecyl isononanoate, isocetyl stearate, isopropyl stearate, isopropyl isostearate, 2-butyl octcanoate, 2-ethylhexyl isostearate (=octylisostearate), cetearyl isononanoate, $C_{12}$–$C_{15}$-alkylbenzoate, $C_{12}$–$C_{15}$-alcohol lactate, glyceryl triisostearate, cyclomethicone, isohexadecane.

The oil components can advantageously be present in an amount of from 0.05 to 80% by weight, based on the total preparation, and are preferably present in an amount of from about 1 to 20% by weight.

The wax component or the totality of the wax components of the novel hydrous, cosmetic sticks is preferably chosen from the group of esters of saturated and/or unsaturated, branched and/or unbranched alkanecarboxylic acids having a chain length of from 1 to 80 carbon atoms and saturated and/or unsaturated, branched and/or unbranched alcohols having a chain length of from 1 to 80 carbons, from the group of esters of aromatic carboxylic acids or hydroxycarboxylic acids (e.g. 12-hydroxystearic acid) and saturated and/or unsaturated, branched and/or unbranched alcohols having a chain length of from 1 to 80 carbon atoms, provided the wax component or the totality of the wax components is a solid at room temperature.

The wax components are preferably chosen from the group of
esters of saturated branched alkanecarboxylic acids having a chain length of from 1 to 60 carbon atoms and saturated unbranched alcohols having a chain length of from 1 to 60 carbon atoms, provided the wax component or the totality of the wax components is a solid at room temperature, and/or of
esters of saturated unbranched alkanecarboxylic acids having a chain length of from 1 to 60 carbon atoms and saturated branched alcohols having a chain length of from 1 to 60 carbon atoms, provided the wax component or the totality of the wax components is a solid at room temperature.

The wax components are particularly preferably chosen from the group of
esters of saturated branched alkanecarboxylic acids having a chain length of from 14 to 44 carbon atoms and saturated branched alcohols having a chain length of from 14 to 44 carbon atoms, provided the wax component or the totality of the wax components is a solid at room temperature.

The wax components may particularly advantageously be chosen from the group of $C_{16-36}$-alkyl stearates, $C_{10-40}$-alkylstearates, $C_{20-40}$-alkylisostearates, $C_{20-40}$-dialkyl dimerates, $C_{18-38}$-alkylhydroxystearoyl stearates, $C_{20-40}$-alkyl erucates and $C_{30-50}$-alkyl beeswax, cetearyl behenate. Silicone waxes such as, for example, stearyl trimethylsilane/stearyl alcohol are also advantageous in some instances.

In particular, vegetable and/or animal waxes or chemically modified derivatives thereof, in particular carnauba wax, candelilla wax, sunflower wax, rice wax, fruit waxes such as orange wax, lemon wax, grapefruit wax, laurel wax (=Bayberry wax) and the like, can be used advantageously. In addition, these natural waxes can also be used alone without synthetic waxes.

The wax components can advantageously be present in an amount of from 0.5 to 80% by weight, based on the total preparation, and are preferably present in an amount of from about 1 to 20% by weight.

It is advantageous to set the ratio of oil and wax components to one another to be approximately in the weight ratio range between 2:1 to 1:2, in particular from 3:2 to 2:3, very particularly preferably about 1:1.

The amount of water can be up to about 85% by weight, based on the total weight of the preparations, optimum water contents usually being chosen in the range between 50 and 75% by weight. If desired, the minimum water content can even be less than 10% by weight. It is, however, of greater advantage for novel emulsion sticks to have a content of greater than 10% by weight of water, particularly when water-soluble or water-dispersible active ingredients such as UV filters and water-dispersible pigments are to be used in concentrations known to the person skilled in the art.

It is also possible to use additional substances which modify the consistency of the novel preparations, for example thickeners, which can be chosen from the group of substances which have at least two hydrophilic radicals, which are joined to one another via a hydrophobic grouping, i.e. conform to the molecular formulae

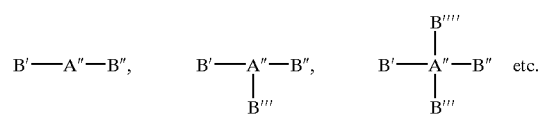

Here, the radicals B with the various indices indicate hydrophilic groups, and the radicals A with the various indices hydrophobic groups.

Such thickeners are preferably chosen from the group of triblock copolymers of the type

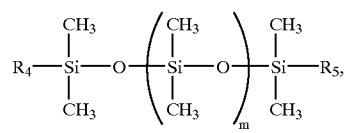

where m can be a number from 10 to 10,000, $R_4$ and $R_5$ may be identical or different and are chosen from the group represented by the general structure

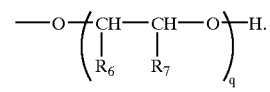

Here, $R_6$ and $R_7$ independently of one another can be chosen such that they are H and methyl, but such that both radicals cannot be methyl at the same time. q is a number from 2 to 1000, preferably from 10 to 200.

$R_4$ and $R_5$ can also be polyol radicals (e.g. glyceryl, polyglyceryl, sorbityl, cellulose radicals etc.).

The stabilizer or the stabilizers are preferably present in concentrations of 0.01–25% by weight, although it is possible and advantageous to keep the content of stabilizers low, for example up to 5% by weight, in each case based on the total weight of the composition.

It can additionally be advantageous to incorporate the customary constituents of cosmetic sticks into the novel preparations, e.g. hydrocarbons, fats and oils for the base substance, and the customary auxiliaries and additives such as perfume oils, preservatives, colour pigments, light protection agents, stabilizers.

Particularly if the novel preparations are to be notable for easy or easier wash-off from human skin, it is advantageous to incorporate into the preparations water-soluble and/or water-swellable polymers, in particular alkyl-etherified cellulose and/or starch derivatives. The following are particularly advantageous: βglucans, xanthan gum, dextrans, hydroxymethylcellulose, hydroxyethylcellulose and/or hydroxypropylcellulose, methoxy-PEG-22/dodecyl glycol copolymers, poloxamers.

Advantageous water-soluble and/or water-swellable polymers can also be chosen to be hydrophilic starch esterified with one or more n-octenylsuccinate radicals. Such starch derivatives are characterized by a structure starch-$X_n$, where X symbolizes the radical

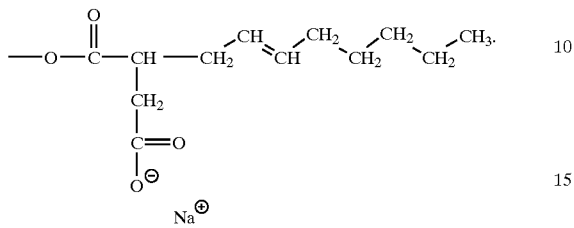

Starch derivatives to be advantageously used according to the invention do not yet have an INCI name (International Nomenclature Cosmetic Ingredient); it would have to officially be "Starch Sodium Octenyl Succinate". Particularly advantageous products are those sold under the name Amiogum®, in particular Amiogum®23 from Cerestar US.

It is preferable for the content of water-soluble and/or water-swellable polymers to be in the concentration range of 0.01–5.0% by weight, particularly preferably 0.1–1.0% by weight.

It has surprisingly been found that the water-soluble and/or water-swellable polymers used according to the invention also increase the gentleness of the novel cosmetic preparations towards the skin. A more pleasant feel is achieved on the skin when the stick composition is applied.

Such water-soluble and/or water-swellable polymers are preferably incorporated by incorporating them into the aqueous phase and adding them together with the aqueous phase, particularly preferably after complete dissolution or swelling, to the molten lipid phase of the preparations.

In addition, it is possible to incorporate the conditioning active ingredients, which do not have to be limited to fat-soluble active ingredients as before, but can also be chosen from the group of water-soluble active ingredients, for example vitamins and the like.

Those cosmetic and dermatological preparations which exist in the form of a sunscreen are also favourable. In addition to the active ingredient combinations according to the invention, these also preferably contain at least one UVA filter substance and/or at least one UVB filter substance and/or at least one inorganic pigment.

However, it is also advantageous for the purposes of the present invention to provide cosmetic and dermatological preparations whose main purpose is not protection against sunlight, but which nevertheless still contain UV protection substances, for example to protect the formulation itself. Thus, for example, UV-A and UV-B filter substances are usually incorporated into day creams.

Preparations according to the invention can advantageously contain substances which absorb UV radiation in the UVB region, the total amount of filter substances being for example from 0.1% by weight to 30% by weight, preferably from 0.5 to 10% by weight, in particular from 1 to 6% by weight, based on the total weight of the preparations, in order to provide cosmetic and/or dermatological preparations which protect the skin from the entire range of ultraviolet radiation. They can also be used as sunscreens.

The UVB filters can be oil-soluble or water-soluble. Examples of oil-soluble substances which may be mentioned are:

3-benzylidenecamphorand derivatives thereof, e.g. 3-(4-methylbenzylidene)camphor, 4-aminobenzoic acid derivatives, preferably 2-ethylhexyl 4-(dimethylamino)benzoate, amyl 4-(dimethylamino) benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methybenzophenone, 2,2'-dihydroxy-4-methoxybenzophenone;

esters of benzalmalonic acid, preferably di(2-ethylhexyl) 4-methoxybenzalmalonate;

2,4,6-trianilino(p-carbo-2'-ethyl-1'-hexyloxy)-1,3,5-triazine

Advantageous water-soluble substances are:

2-phenylbenzimidazole-5-sulphonicacid and salts thereof, for example sodium, potassium or triethanolammonium salts, sulphonic acid derivatives of benzophenones, preferably 2-hydroxy-4-methoxybenzophenone-5-sulphonicacid and its salts;

sulphonic acid derivatives of 3-benzylidenecamphor, such as, for example, 4-(2-oxo-3-bornylidenemethyl) benzenesulphonicacid, 2-methyl-5-(2-oxo-3-bornylidenemethyl)sulphonicacid and its salts.

The list of given UVB filters which can be used according to the invention is of course not intended to be limiting.

It can also be advantageous to use UVA filters which are usually present in cosmetic and/or dermatological preparations in the preparations according to the invention. Such filter substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. Preparations which contain these combinations are also provided by the invention. The amounts of UVA filter substances used are the same as those which have been given for UVB filter substances.

Cosmetic and/or dermatological preparations according to the invention can also contain inorganic pigments which are usually used in cosmetics for protecting the skin against UV rays. These are oxides of titanium, zinc, iron, zirconium, silicon, manganese, aluminium, cerium and mixtures thereof, and modifications in which the oxides are the active agents. Particular preference is given to pigments based on titanium dioxide. The quantities given for the above combinations can be used.

The novel water-rich sticks are also excellent vehicles for dermatological active ingredients. In particular, they are suitable carriers for substances effective against acne. It is thus advantageous to add substances which are effective against acne to the preparations used according to the invention, for example substances effective against *Propionibacterium acnes* (for example those described in DE-A 42 29 707, DE-A 43 05 069, DE-A 43 07 976, DE-A 43 37 711, DE-A 43 29 379) but also other substances effective against acne, for example all-trans-retinoic acid, 13-cis-retinoic acid and related substances, or anti-inflammatory active ingredients, for example batyl alcohol (α-octadecyl glyceryl ether), selachyl alcohol (α-9-octadecenyl glyceryl ether), chimyl alcohol (α-hexadecyl glyceryl ether) and/or bisabolol.

The amount of antiacne agents (one or more compounds) in the preparations is preferably from 0.01 to 30% by weight, particularly preferably 0.1–20% by weight, in particular 1–10% by weight, based on the total weight of the preparation.

Advantageous active ingredients are also antioxidants, in particular those which are able to protect not only the constituents of the formulation, but also the skin against oxidative stress.

The preparations thus advantageously comprise one or more antioxidants. Favourable, but nevertheless optional, antioxidants are all antioxidants which are suitable or customary for cosmetic and/or dermatological applications. It is advantageous to use antioxidants as a single class of active ingredient, for example when a cosmetic or dermatological use is of particular interest, such as the combating of oxidative stress of the skin. It is, however, also favourable for the novel W/O emulsion sticks to contain one or more antioxidants when the preparations are intended to be used for another purpose, e.g. as deodorants or sunscreens.

The antioxidants are particularly advantageously chosen from the group consisting of amino acids (for example glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and other thiols (e.g. thioglycerol, thiosorbitol, thioglycolic acid, thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very small tolerated doses (e.g. pmol to $\mu$mol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitates, Mg ascorbyl phosphates, ascorbyl acetates), isbascorbic acid and derivatives thereof, tocopherols and derivatives (e.g. vitamin E acetate), vitamin A and derivatives (vitamin A palmitate) and coniferylbenzoate of benzoin, rutinic acid and derivatives thereof, ferulic acid and derivatives thereof, butylated hydroxytoluene, butylated hydroxyanisole, nordihydroguaiac resin acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenium methionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

For the purposes of the present invention, although it is particularly advantageous to use oil-soluble or oil-dispersible antioxidants, it has been found that the invention opens up possibilities when water-soluble or water-dispersible antioxidants are used in stick formulations.

The amount of antioxidants (one or more compounds) in the preparations is preferably from 0.001 to 30% by weight, particularly preferably 0.05–20% by weight, in particular 1–10% by weight, based on the total weight of the preparation.

If vitamin E and/or derivatives thereof are used as the antioxidant(s), it is advantageous to choose their respective concentrations from the range 0.001–10% by weight, based on the total weight of the formulation.

If vitamin A or vitamin A derivatives, or carotenes or derivatives thereof are the antioxidant(s), it is advantageous to choose their respective concentrations from the range 0.001–10% by weight, based on the total weight of the formulation.

The person skilled in the art is of course aware that demanding cosmetic preparations are in most cases inconceivable without the customary auxiliaries and additives. These include, for example, consistency regulators, fillers, perfume, dyes, emulsifiers, additional active ingredients such as vitamins or proteins, light protection agents, stabilizers, insect repellents, alcohol, water, salts, antimicrobial, proteolytic or keratolytic substances, etc.

According to the invention, active ingredients can also be very advantageously chosen from the group consisting of lypophilic active ingredients, in particular from the following group:

acetyl salicylic acid, atropine, azulene, hydrocortisone and derivatives thereof, e.g. hydrocortisone-17-valerate, vitamins, e.g. ascorbic acid and derivatives thereof, vitamins of the B and D groups, very favourably vitamin $B_1$, vitamin $B_{12}$, vitamin $D_1$, but also bisabolol, unsaturated fatty acids, namely the essential fatty acids (often also called vitamin F), in particular γ-linolenic acid, oleic acid, eicosapentanoic acid, docosahexanoic acid and derivatives thereof, chloramphenicol, caffeine, prostaglandins, thymol, camphor, extracts or other products of vegetable and animal origin, e.g. evening primrose oil, starflower oil or currant seed oil, fish oils, cod-liver oil or also ceramides and ceramide-like compounds etc.

It is also advantageous to choose the active ingredients from the group of refatting substances, for example Purcellinöl®, Eucerit® and Neocerit®.

The sticks according to the invention also contribute in an advantageous manner to skin smoothing, particularly when they contain one or more substances which promote skin smoothing.

It is optionally possible and advantageous to use the preparations according to the invention as bases for pharmaceutical formulations. Corresponding requirements apply mutatis mutandis to the formulation of medicinal preparations. The transitions between pure cosmetics and pure pharmaceuticals are fluid. According to the invention, suitable pharmaceutical active ingredients are, in principle, all classes of active ingredient, with lipophilic active ingredients being preferred. Examples are: antihistamines, antiphlogistics, antibiotics, antimycotics, circulation-promoting active ingredients, keratolytics, hormones, steroids, vitamins etc.

Unless stated otherwise, all amounts, percentages or parts refer to the weight, in particular to the total weight of the preparations or of the respective mixtures.

The examples below serve to illustrate the invention without limiting it.

EXAMPLE 1

Sunscreen stick with a high water content

| | % by weight |
|---|---|
| Polyglyceryl-3 diisostearate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3HEDTA$ | 2.000 |

EXAMPLE 2

Sunscreen stick with a high water content

| | % by weight |
|---|---|
| PEG-45/dodecyl glycol copolymer | 0.900 |
| Polyglyceryl-3 diisostearate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Methylbenzylidenecamphor | 4.000 |
| Titanium dioxide | 2.000 |
| $C_{20-40}$-alkyl stearate | 15.000 |
| Glycerol | 2.000 |
| $Na_3HEDTA$ | 2.000 |
| Water | ad 100.000 |

EXAMPLE 3

Sunscreen stick with a high water content

| | % by weight |
|---|---|
| PEG-45/dodecyl glycol copolymer | 0.900 |
| Polyglyceryl-3 diisostearate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Titanium dioxide | 2.000 |
| Sodium hydroxide solution | 0.200 |
| $C_{20-40}$-alkyl stearate | 15.000 |
| Glycerol | 2.000 |
| $Na_3HEDTA$ | 2.000 |
| Water | ad 100.000 |

EXAMPLE 4

Sunscreen stick with a high water content

| | % by weight |
|---|---|
| PEG-45/dodecyl glycol copolymer | 0.900 |
| Polyglyceryl-3 diisostearate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Methylbenzylidenecamphor | 4.000 |
| Titanium dioxide* and propylene glycol | 2.000 |
| Sodium hydroxide solution | 0.200 |
| $C_{20-40}$-alkyl stearate | 15.000 |
| Glycerol | 2.000 |
| Water | ad 100.000 |

*Water-dispersible titanium dioxide: Tioveil AQ + 10% propylene glycol from Tioxid Specialities

EXAMPLE 5

Sunscreen stick with a high water content

| | % by weight |
|---|---|
| PEG-45/dodecyl glycol copolymer | 0.900 |
| 2-ethylhexyl glycerol ether | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Methylbenzylidenecamphor | 4.000 |
| Titanium dioxide* and propylene glycol | 2.000 |
| Sodium hydroxide solution | 0.200 |
| $C_{20-40}$-alkyl stearate | 15.000 |
| Glycerol | 2.000 |
| $Na_3HEDTA$ | 2.000 |
| Water | ad 100.000 |

*Water-dispersible titanium dioxide: Tioveil AQ + 10% propylene glycol from Tioxid Specialities

EXAMPLE 7

Sunscreen stick with a high water content

| | % by weight |
|---|---|
| PEG-45/dodecyl glycol copolymer | 0.900 |
| Sorbitan isostearate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3HEDTA$ | 2.000 |
| Water | ad 100.000 |

EXAMPLE 8

Sunscreen stick with a high water content

| | % by weight |
|---|---|
| PEG-45/dodecyl glycol copolymer | 0.900 |
| Pentaerythrityl isostearate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3$HEDTA | 2.000 |
| Water | ad 100.000 |

EXAMPLE 9

Sunscreen stick with a high water content

| | % by weight |
|---|---|
| PEG-45/dodecyl glycol copolymer | 0.900 |
| PEG-7 hydrogenated castor oil | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3$HEDTA | 2.000 |
| Water | ad 100.000 |

EXAMPLE 10

Sunscreen stick with a high water content

| | % by weight |
|---|---|
| PEG-45/dodecyl glycol copolymer | 0.900 |
| Polyglyceryl-2 dipolyhydroxystearate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3$HEDTA | 2.000 |
| Water | ad 100.000 |

EXAMPLE 11

Sunscreen stick with a high water content

| | % by weight |
|---|---|
| PEG-45/dodecyl glycol copolymer | 0.900 |
| PEG-40 sorbitan perisostearate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3$HEDTA | 2.000 |
| Water | ad 100.000 |

EXAMPLE 12

Sunscreen stick with a high water content

| | % by weight |
|---|---|
| PEG-45/dodecyl glycol copolymer | 0.900 |
| Isostearyl diglycerol succinate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3$HEDTA | 2.000 |
| Water | ad 100.000 |

EXAMPLE 13

Sunscreen stick with a high water content

| | % by weight |
|---|---|
| PEG-45/dodecyl glycol copolymer | 0.900 |
| Glycerol isostearate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3$HEDTA | 2.000 |
| Water | ad 100.000 |

EXAMPLE 14

Sunscreen stick with a high water content

| | % by weight |
|---|---|
| PEG-45/dodecyl glycol copolymer | 0.900 |
| Cetyl alcohol | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3$HEDTA | 2.000 |
| Water | ad 100.000 |

EXAMPLE 15

Sunscreen stick with a high water content

| | % by weight |
|---|---|
| PEG-45/dodecyl glycol copolymer | 0.900 |
| Propylene glycol diisostearate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3$HEDTA | 2.000 |
| Water | ad 100.000 |

EXAMPLE 16

Sunscreen stick with a high water content

| | % by weight |
|---|---|
| PEG-45/dodecyl glycol copolymer | 0.900 |
| Isostearyl glycerol ether | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3$HEDTA | 2.000 |
| Water | ad 100.000 |

EXAMPLE 17

Sunscreen stick with a high water content

| | % by weight |
|---|---|
| PEG-45/dodecyl glycol copolymer | 0.900 |
| Glycerol sorbitan isostearate | 1.800 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 15.000 |
| Glycerol | 2.000 |
| $Na_3$HEDTA | 2.000 |
| Water | ad 100.000 |

EXAMPLE 18

Antiacne stick with a high water content

| | % by weight |
|---|---|
| Polyglyceryl-3 diisostearate | 1.600 |
| Glyceryl caprate | 1.000 |
| Caprylic/capric triglycerides | 4.000 |
| Octyldodecanol | 4.000 |
| Dicaprylyl ether | 4.000 |
| Cetearyl behenate | 6.000 |
| Salicylic acid | 1.000 |
| Octacosanyl stearate | 6.000 |
| Glycerol | 2.000 |
| Water | ad 100.000 |

EXAMPLE 19

Antiacne stick with a high water content

| | % by weight |
|---|---|
| Polyglyceryl-3 diisostearate | 1.600 |
| Glyceryl caprate | 1.000 |
| Caprylic/capric triglycerides | 4.000 |
| Octyldodecanol | 4.000 |
| Dicaprylyl ether | 4.000 |
| Cetearyl behenate | 6.000 |
| Salicylic acid | 1.000 |
| Octacosanyl stearate | 6.000 |
| Glycerol | 2.000 |
| Water | ad 100.000 |

EXAMPLE 20

Antiacne stick with a high water content

| | % by weight |
|---|---|
| Polyglyceryl-3 diisostearate | 1.600 |
| Azelaic acid | 2.000 |
| Caprylic/capric triglycerides | 4.000 |
| Octyldodecanol | 4.000 |
| Dicaprylyl ether | 4.000 |

EXAMPLE 21 (continued)

Antiacne stick with a high water content

|  | % by weight |
|---|---|
| Cetearyl behenate | 6.000 |
| Octacosanyl stearate | 6.000 |
| Glycerol | 2.000 |
| Water | ad 100.000 |

EXAMPLE 21

Antiacne stick with a high water content

|  | % by weight |
|---|---|
| Polyglyceryl-3 diisostearate | 1.600 |
| Wool wax acid | 2.000 |
| Caprylic/capric triglycerides | 4.000 |
| Octyldodecanol | 4.000 |
| Dicaprylyl ether | 4.000 |
| Cetearyl behenate | 6.000 |
| Octacosanyl stearate | 6.000 |
| Water | ad 100.000 |

EXAMPLE 22

Antiacne stick with a high water content

|  | % by weight |
|---|---|
| Polyglyceryl-3 diisostearate | 1.600 |
| Azelaic acid | 2.000 |
| Caprylic/capric triglycerides | 4.000 |
| Octyldodecanol | 4.000 |
| Dicaprylyl ether | 4.000 |
| Cetearyl behenate | 6.000 |
| Octacosanyl stearate | 6.000 |
| Glycerol | 2.000 |
| Water | ad 100.000 |

EXAMPLE 23

Antiacne stick with a high water content

|  | % by weight |
|---|---|
| Polyglyceryl-3 diisostearate | 1.600 |
| Azelaic acid | 2.000 |
| Caprylic/capric triglycerides | 4.000 |
| Octyldodecanol | 4.000 |
| Dicaprylyl ether | 4.000 |
| Cetearyl behenate | 6.000 |
| Octacosanyl stearate | 6.000 |
| Glycerol | 2.000 |
| Water | ad 100.000 |

EXAMPLE 24

Antiacne stick with a high water content

|  | % by weight |
|---|---|
| Polyglyceryl-3 diisostearate | 1.600 |
| Benzoyl peroxide | 2.000 |
| Caprylic/capric triglycerides | 4.000 |
| Octyldodecanol | 4.000 |
| Dicaprylyl ether | 4.000 |
| Cetearyl behenate | 6.000 |
| Octacosanyl stearate | 6.000 |
| Glycerol | 2.000 |
| Water | ad 100.000 |

EXAMPLE 25

Lipstick with a high water content

|  | % by weight |
|---|---|
| Polyglyceryl-3 diisostearate | 1.600 |
| iron oxide | 2.000 |
| Caprylic/capric triglycerides | 4.000 |
| Octyldodecanol | 4.000 |
| Dicaprylyl ether | 4.000 |
| Cetearyl behenate | 6.000 |
| Titanium dioxide | 2.000 |
| Octacosanyl stearate | 6.000 |
| Glycerol | 2.000 |
| Water | ad 100.000 |

EXAMPLE 26

Lipstick with a high water content

|  | % by weight |
|---|---|
| Polyglyceryl-3 diisostearate | 1.600 |
| Cholesteryl alcohol | 2.000 |
| Caprylic/capric triglycerides | 4.000 |
| Octyldodecanol | 4.000 |
| Dicaprylyl ether | 4.000 |
| Cetearyl behenate | 6.000 |
| Titanium dioxide | 2.000 |
| Octacosanyl stearate | 6.000 |
| Glycerol | 2.000 |
| Water | ad 100.000 |

EXAMPLE 27

Sunscreen stick with a high water content

|  | % by weight |
|---|---|
| Polyglyceryl-3 diisostearate | 1.600 |
| Caprylic/capric triglycerides | 5.000 |
| Octyldodecanol | 5.000 |
| Dicaprylyl ether | 5.000 |
| Butylmethoxydibenzoylmethane | 2.000 |
| Phenylbenzimidazolesulphonic acid | 4.000 |
| Sodium hydroxide solution | 0.200 |
| Titanium dioxide | 2.000 |
| $C_{20-40}$-alkyl stearate | 13.000 |

-continued

Sunscreen stick with a high water content

| | % by weight |
|---|---|
| Orange wax | 2.000 |
| Glycerol | 2.000 |
| Na₃HEDTA | 2.000 |
| Water | ad 100.000 |

What is claimed is:

1. Cosmetic sticks selected from the group consisting of lipsticks, antiacne sticks, sunscreen sticks and eyeshadow sticks, which are comprised of:
    (a) a lipid phase, which comprises
        (a1) at least one oil component
        (a2) at least one wax component
        (a3) optionally other substances soluble or dispersible in the lipid phase,
    (b) an aqueous phase, which comprises
        (b1) from 50 to 75% by weight of water, based on the total weight of the stick composition and
        (b2) optionally other substances soluble or dispersible in water,
    (c) optionally one or more active ingredients for lipsticks, antiacne sticks, sunscreen sticks and eyeshadow sticks,
    (d) a W/O emulsifier or a mixture of two or more W/O emulsifers, selected from the group consisting of surface-active substances of the structure A—B—A', where A and A' are identical or different hydrophobic organic radicals, and B is a hydrophilic group,
    (e) optional surface-active substances as coemulsifiers, stabilizer, and cosmetic and/or pharmaceutical auxiliaries, active ingredients and/or additives.

2. Lipsticks, antiacne sticks, sunscreen sticks and eyeshadow sticks according to claim 1, wherein the W/O emulsifier or the W/O emulsifiers are selected from the group of substances of the formula

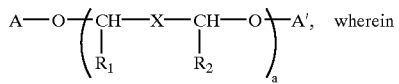

A and A' are identical or different hydrophobic organic radicals,
a is a number from 1 to 100,
X is a single bond or the group

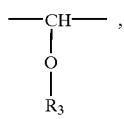

R and R₂ independently of one another are chosen from the group consisting of H or methyl, but such that the two radicals are not methyl at the same time,
R₃ is chosen from the group consisting of H and the branched and unbranched, saturated and unsaturated alkyl and acyl radicals having 1–20 carbon atoms,
or that the W/O emulsifier(s) is/are chosen from the group of fatty alcohols having 8–30 carbon atoms, monoglycerol esters of saturated and/or unsaturated, branched and/or unbranched alkanecarboxylic acids having a chain length of 8–24, diglycerol esters of saturated and/or unsaturated, branched and/or unbranched alkanecarboxylic acids having a chain length of 8–24, triglycerol esters of saturated and/or unsaturated, branched and/or unbranched alkanecarboxylic acids having a chain length of 8–24, polyglycerol esters of saturated and/or unsaturated, branched and/or unbranched alkanecarboxylic acids having a chain length of 8–24, and up to 10 glycerol units, monoglycerol ethers of saturated and/or unsaturated, branched and/or unbranched alcohols having a chain length of 8–24, diglycerol ethers of saturated and/or unsaturated, branched and/or unbranched alcohols having a chain length of 8–24, triglycerol ethers of saturated and/or unsaturated, branched and/or unbranched alcohols having a chain length of 8–24, polyglycerol ethers of saturated and/or unsaturated, branched and/or unbranched alkanecarboxylic acids having a chain length of 8–24, and up to 10 glycerol units, propylene glycol esters of saturated and/or unsaturated, branched and/or unbranched alkanecarboxylic acids having a chain length of 8–24, sorbitan esters of saturated and/or unsaturated, branched and/or unbranched alkanecarboxylic acids having a chain length of 8–24, sorbitan esters of polyols, pentaerythritol esters of saturated and/or unsaturated, branched and/or unbranched alkanecarboxylic acids having a chain length of 8–24, methylglucose esters of saturated and/or unsaturated, branched and/or unbranched alkanecarboxylic acids having a chain length of 8–24, polyglycerol methylglucose esters of saturated and/or unsaturated, branched and/or unbranched alkanecarboxylic acids having a chain length of 8–24, or that the abovementioned types of W/O emulsifiers are additionally polyethoxylated and/or polypropoxylated such that they are ethoxylated and/or propoxylated W/O emulsifers.

3. Lipsticks, antiacne sticks, sunscreen sticks and eyeshadow sticks according to claim 2, wherein the W/O emulsifier or the W/O emulsifiers is/are radicals A and A' which are chosen from the group consisting of branched and unbranched, saturated and unsaturated alkyl and acyl radicals, hydroxyacyl radicals having 10–30 carbon atoms and hydroxyacyl groups joined together via ester functions, according to the formula

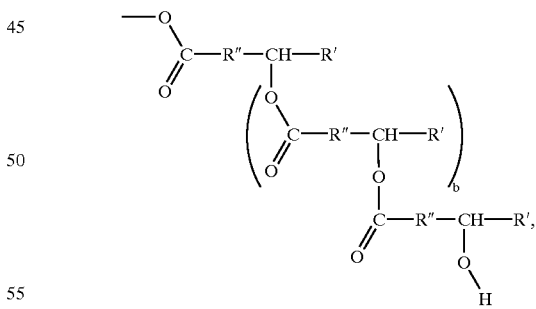

where R' are branched and unbranched alkyl groups having from 1 to 20 carbon atoms, and R" are branched and unbranched alkylene groups having from 1 to 20 carbon atoms, and b can assume numbers from 0 to 200.

4. Lipsticks, antiacne sticks, sunscreen sticks and eyeshadow sticks according to claim 1, wherein the W/O emulsifier(s) is/are chosen from the group consisting of PEG-30 dipolyhydroxystearate, decaglyceryl heptaoleate, polyglyceryl-3 diisostearate, PEG-8 distearate, diglycerol dipolyhydroxystearate.

5. Lipsticks, antiacne sticks, sunscreen sticks and eyeshadow sticks according to claim 1, wherein the stabilizer(s) is/are chosen from the group of substances of the formula

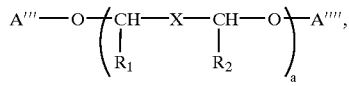

wherein
A''' and A'''' are identical or different hydrophobic organic radicals,
a is a number from 1 to 100,
X is a single bond or the group

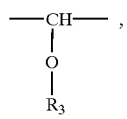

$R_1$ and $R_2$ independently of one another are selected from the group consisting of H and methyl, but such that the two radicals are not methyl at the same time,
$R_3$ is selected from the group consisting of H and the branched and unbranched, saturated and unsaturated alkyl and acyl radicals having 1–20 carbon atoms,
wherein the radicals A''' and A'''' can be identical or different and are from the group consisting of

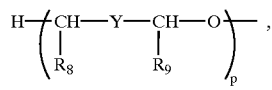

where $R_8$ and $R_9$ can be identical or different and are from the group consisting of saturated and unsaturated alkyl and acyl radicals having 1–30 carbon atoms, p is a number from 1 to 20, and Y is a single bond or the group

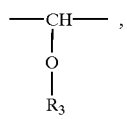

where $R_3$ is selected from the group consisting of H and the branched and unbranched, saturated and unsaturated alkyl and acyl radicals having 1–30 carbon atoms, alkyl radicals or acyl radicals.

6. Lipsticks, antiacne sticks, sunscreen sticks and eyeshadow sticks according to claim 5, wherein the stabilizer used is the PEG-45/dodecyl glycol copolymer and/or the PEG-22/dodecyl glycol copolymer and/or the methoxy-PEG-22/dodecyl glycol copolymer.

7. Lipsticks, antiacne sticks, sunscreen sticks and eyeshadow sticks according to claim 1, wherein the oil component or the totality of the oil components of the sticks is selected from the group consisting of esters of saturated and/or unsaturated, branched and/or unbranched alkanecarboxylic acids having a chain length of from 14 to 44 carbon atoms, saturated and/or unsaturated, branched and/or unbranched alcohols having a chain length of from 14 to 44 carbon atoms, esters of aromatic carboxylic acids and saturated and/or unsaturated, branched and/or unbranched alcohols having a chain length of from 3 to 30 carbon atoms, provided the oil component or the totality of the oil components is a liquid at room temperature.

8. Lipsticks, antiacne sticks, sunscreen sticks and eyeshadow sticks according to claim 1, wherein the oil component or the totality of the oil components of the sticks are selected from the group consisting of branched and unbranched hydrocarbons, cyclic or linear silicone oils, dialkyl ethers, saturated or unsaturated, branched alcohols, and synthetic or natural triglycerol esters of saturated and/or unsaturated, branched and/or unbranched alkanecarboxylic acids having a chain length of from 8 to 24.

9. Lipsticks, antiacne sticks, sunscreen sticks and eyeshadow sticks according to claim 1, wherein the wax component or the totality of the wax components of the sticks are selected from the group consisting of esters of saturated and/or unsaturated, branched and/or branched alkanecarboxylic acids having a chain length of from 1 to 80 carbon atoms, saturated and/or unsaturated, branched and/or unbranched alcohols having a chain length of from 1 to 80 carbon atoms, esters of aromatic carboxylic acids and saturated and/or unsaturated, branched and/or unbranched alcohols having a chain length of from 1 to 80 carbon atoms, provided that the wax component or the totality of the wax components is a solid at room temperature.

10. Lipsticks, antiacne sticks, sunscreen sticks and eyeshadow sticks according to claim 1, which additionally contains one or more water-soluble and/or water-swellable polymers.

11. Lipsticks, antiacne sticks, sunscreen sticks and eyeshadow sticks according to claim 2, wherein a is a number from 2 to 60.

12. Lipsticks, antiacne sticks, sunscreen sticks and eyeshadow sticks according to claim 2, wherein a is a number from 5 to 40.

13. Lipsticks, antiacne sticks, sunscreen sticks and eyeshadow sticks according to claim 5, wherein a is a number from 2 to 60.

14. Lipsticks, antiacne sticks, sunscreen sticks and eyeshadow sticks according to claim 10, wherein said one or more water-soluble and/or water-swellable polymers are alkyl-etherified cellulose and/or starch derivatives selected from the group consisting of β-glucans, xanthan gum, dextrans, hydroxymethylcellulose, hydroxyethylcellulose and/or hydroxypropylcellulose, methoxy PEG-22/dodecyl glycol copolymers, poloxamers, hydrophilic starch esterified with one or more n-octenylsuccinate radicals.

15. The cosmetic sticks of claim 1, wherein the lipid phase (a) is present in an amount from 1 to 20% by weight, based on the total weight of the preparation.

16. The cosmetic sticks of claim 1, wherein the weight of water in the aqueous phase (b) is from 50 to 75% by weight, based on the total weight of the cosmetic sticks.

17. The cosmetic sticks of claim 15, wherein the weight of water in the aqueous phase (b) is from 50 to 75% by weight, based on the total weight of the cosmetic sticks.

* * * * *